United States Patent [19]

Seifter et al.

[11] Patent Number: 4,491,574

[45] Date of Patent: Jan. 1, 1985

[54] REDUCTION OF HIGH DOSE ASPIRIN TOXICITY BY DIETARY VITAMIN A

[75] Inventors: Eli Seifter, New Hyde Park; Giuseppe Rettura, Bronx, both of N.Y.

[73] Assignee: Albert Einstein College of Medicine of Yeshiva University, a division of Yeshiva University, Bronx, N.Y.

[21] Appl. No.: 471,498

[22] Filed: Mar. 2, 1983

[51] Int. Cl.$^3$ .................. A61K 31/605; A61K 31/615
[52] U.S. Cl. ...................................... 424/10; 424/233; 424/235
[58] Field of Search ........................... 424/10, 233, 235

[56] References Cited

U.S. PATENT DOCUMENTS 3,966,967  6/1976  Lee .......................................  424/318
4,182,770  1/1980  Behpour et al. ................. 424/273 P Primary Examiner—Stanley J. Friedman

[57] ABSTRACT

The present invention is directed to a development for alleviating the adverse side-effects of taking non-steroid analgesics and anti-inflammatory agents such as aspirin, by also ingesting vitamin A (or B-carotene) formulations. It has been found that vitamin A ingestion has a salutary and therapeutic effect, in that the vitamin A decreases toxicity, including ulcerogenesis, due to ingestion of such agents, e.g. aspirin. Aspirin per se is a very effective medication with pronounced analgesic properties, including the temporary relief of minor aches and pains, and is widely used (in small amounts) with no ill effects. However, since aspirin is a mild anti-coagulant, it sometimes causes bleeding of stomach ulcers, or aggravates pre-existing conditions of that nature. Thus the concomitant administration of vitamin A per se to humans taking aspirin is very effective in decreasing toxicity and inhibiting ulcerogenesis and bleeding in the stomach. Also effective, but less so, is B-carotene, a vitamin A precursor, which when assimilated into the body yields vitamin A or a derivative thereof.

15 Claims, No Drawings

REDUCTION OF HIGH DOSE ASPIRIN TOXICITY BY DIETARY VITAMIN A

BACKGROUND OF THE INVENTION

1. Field of the Invention

The decrease or reduction of toxicity, and the inhibition of ulcerogenesis and bleeding in the stomach, due to the ingestion of a pharmaceutically effective concentration or dosage of aspirin.

2. Description of the Prior Art

The extensive use of aspirin (acetyl salicylic acid) in medicine as an analgesic and as an anti-inflammatory agent or antipyretic is well known. Aspirin is used not only to treat various medical conditions, such as the alleviation of pain due to rheumatic and arthritic diseases, but is also used for temporary relief of minor aches and pains, colds misery, common or nervous tension headache, fever, etc. It has recently been established that, on a statistical basis, aspirin when regularly ingested is very effective in preventing strokes and heart attacks, especially in middle-aged men, evidently because of its mildly anti-coagulant properties, which tend to inhibit or prevent blood clots and improve circulation.

Aspirin is outstanding with respect to its low cost, safety, reliability, and almost universal effectiveness, and therefore is the medicine of choice for a number of conditions. Aspirin has also been suggested for usage as a growth stimulant in animal feeds, e.g. for stimulating the growth of ruminants, e.g. cattle, poultry, and swine, see U.S. Pat. No. 3,147,120.

Pharmaceutical compositions and the like containing aspirin as a component or ingredient have been suggested in U.S. Pat. Nos. 3,039,927; 4,113,856; 3,312,593; 3,928,588; 3,937,801; 4,153,691; 4,228,161; and 4,228,162.

Basically, and from a clinical viewpoint, the prognosis for aspirin therapy in most human subjects is good, especially if relatively low dosages of the aspirin are indicated. However, in some instances, and especially when the ingestion of a pharmaceutically effective high dosage or concentration of aspirin is prescribed, e.g. to alleviate the pain and suffering due to rheumatoid arthritis, the indicated aspirin therapy causes stomach ulceration, ischemia, or at least bleeding in the upper gastro-intestinal tract following oral administration. In most cases, such bleeding is so slight as to be harmless, but it can be a major problem in some patients, especially those who regularly take high doses, for example those who suffer from rheumatoid disease.

Thus aspirin, which exhibits a unique combination of effects on anti-inflammatory, antipyretic, and analgesic treatments, is perhaps the most popular and effective non-prescription analgesic drug. However, it has been cautioned that aspirin ingestion can cause severe gastrointestinal bleeding in users and particularly in patients with gastro-intestinal lesions (P. R. Holt, Proc. Soc. Exp. Biol. Med., 102, 517 (1959); P. H. N. Wood, S. E. A. Harvey, and A. Dixon, Brit. Med. J., 1,669 (1962); M. I. Grossman, K. K. Matsumote, and R. J. Lichter, Gastro-enterology, 40, 383 (1961)). Although the mechanism by which the blood is lost is still unclear, studies (J. R. Leonards and G. Levy, J. Pharm. Sci., 58. 1277 (1969); and A. Weiss, E. R. Pitman, and E. C. Graham, Amer. J. Med., 31,266 (1961)), have shown that aspirin, when given orally in a liquid form or when given intravenously, produces no occult bleeding. On the other hand, aspirin tablet are found to cause gastric bleeding particularly when tablets disintegrate slowly and remain in the stomach as large tablet fragments. These results suggest that the gastric irritation by aspirin may be greatly reduced by reducing the particle size of the drug. The reduction of the drug particle size in the gastro-intestinal fluid may be best achieved by using a liquid dosage form. Hence, many attempts have been made to formulate a stable aspirin solution to reduce the undesirable side effect (H. R. Mehta and F. G. Drommond; J. Amer. Phar. Assoc. Pract. Ed., 15, 103 (1954); H. W. Tomski and L. S. Waller, Pharm. J., 144, 53 (1940); M. Farges, U.S. Pat. No. 3,316,150, Feb. 26, 1964; L. A. Luzzi, D. W. Whitworth, and H. W. Jun., J. Pharm. Sci., 62, 1184 (1973); and T. W. Schwarz, N. G. Suhvemar, and R. G. Renaldi, J. Amer. Pharm. Assoc. Pract. Ed., 19, 40 (1958)).

Thus, acute and chronic aspirin poisoning are important health and safety problems; there is therefore a need to develop antidotes having either preventive or therapeutic actions. Excessive aspirin ingestion may even cause death, or at least may cause ulcerogenesis or significant morbidity, manifested by reduced body weight gain, severe stomach distention, marked thinning of the forestomach, and severe blanching of the stomach wall, together with multiple severe gastric ulceration. In summary, in aspirin poisoning, like in stress ulceration induced by trauma, the stomach tissue has an abnormal coloration. Usually the stomach has a pinkish complexion due to blood contained in the capillaries that course the tissue. In the stressed or aspirin poisoned rat, the stomach looks dead white, due to the fact that during stress and aspirin poisoning the small blood vessels to the stomach are narrowed, thereby preventing blood flow to the cells of the stomach. As a consequence of this deprivation, stomach cells are prevented from getting adequate nutrients and oxygen that they normally get from blood. A secondary consequence is that nutrient and energy-deprived cells cannot prevent certain thermal or diffusion processes (acid) from occurring; furthermore, blood-starved tissues cannot synthesize components such as mucus that help maintain stomach cells in an environment that would, otherwise, digest them away. Another aspect of aspirin toxicity is the G.I. distension that occurs due to inhibited smooth muscle activity.

The use of various compounds, particularly salicylic acid derivatives, to combat the gastrointestinal ulceration associated with use of various anti-inflammatory drugs, is known. See, for example, (1) Hanchar et al, "Antiulcer Effect of Aspirin," Gastroenterology, Vol. 72, No. 5, Part 2 (1977), which reports the protective effect of aspirin, sodium salicylate, and aminopyrine when used with indomethacin; (2) British Pat. No. 1,483,165, which describes anti-flammatory compositions having decreased gastrointestinal side-effects comprising indomethacin or other anti-inflammatory agents together with salicylic acid or an alkali metal salicylate; (3) U.S. Pat. No. 4,016,268 which describes the use of bismuth subsalicylate co-administered with anti-inflammatory drugs to combat gastric ulceration associated with such drugs; (4) Robert and Asano, Prostaglandins, Vol. 14, No. 2, pp. 333–338 (1977), which describes the use of 16, 16-dimethyl $PGE_2$ to prevent intestinal lesions from indomethacin in experimental animals; (5) Japanese Patent Publication No. 5 3062 839 which discloses the use of mepirizole with non-steroidal anti-inflammatory agents to reduce ulcer formation caused by the latter; (6) Rainsford, Agents and Actions, Vol. 7, 516, pp. 573–577 (1977), which describes that while the mixture of indomethacin and probenecid is effective in reducing the gastric damage by indomethacin, the effect of aspirin and indomethacin is almost additive; (7) Goburdhum et al, J. Pharm. Methods., Vol. 1, pp. 109–114 (1978), which discloses that copper salicylate is more effective than sodium salicylate in achieving inhibition of the ulcerogenic effects of indomethacin; (8) U.S. Pat. No. 4,066,756, which discloses the use of sodium cromoglycate to inhibit the gastrointestinal irritation caused by indomethacin; and (9) Scrip, Oct. 14, 1973, p. 24, which discloses the use of parsalamide or rimazolium methylsulfate to reduce the ulcerogenic potential of indomethacin. However, unlike the majority of co-administered agents described in the prior art, particularly sodium salicylate and aspirin, the phenyl benzoic acid compounds are, surprisingly, many times more effective on a molar basis. Gastric ulceration in the rat has also been shown to be inhibited by salicylic acid or aspirin alone. See Pauls et al., Science, Jan. 2, 1948. Also pertinent are U.S. Pat. Nos. 2,283,817 and 4,292,298.

SUMMARY OF THE INVENTION

1. Purposes of the Invention

It is an object of the present invention to provide an improvement in aspirin therapy.

Another object is to alleviate or prevent undesirable side-effects, such as ulcerogenesis and stomach ulceration, ischemia and gastro-intestinal bleeding, or the like, due to aspirin oral ingestion.

A further object is to reduce high dose aspirin toxicity by dietary vitamin A.

An additional object is to utilize vitamin A ingestion to provide a salutary benefit to those ingesting aspirin, by counter-acting and preventing the toxic effects of aspirin therapy.

Still another object is to decrease, reduce, or eliminate toxicity, and to inhibit ulcerogenesis and bleeding in the stomach, due to the oral ingestion of a pharmaceutically effective concentration or dosage of aspirin.

Still a further object is to provide a synergistic aspirin formulation comprising aspirin together with a small but effective amount of vitamin A.

Yet another object is to extend the benefits of aspirin therapy to human subjects and patients who, because of pre-existing conditions, dispositions, or organic nature, were prevented from taking, ingesting, or assimilating aspirin in the past.

Still another object is to employ vitamin A to boost the immunity of human patients suffering from various diseases, so that they can take and assimilate aspirin by oral ingestion, or so that the aspirin is permitted to be effective and take effect medically without side effects.

An object is to medically use the combination of aspirin and vitamin A in a human subject, so that the aspirin exerts pain-relieving properties without causing toxicity to the stomach.

Another object is to alleviate or prevent adverse side effects due to the oral ingestion of aspirin.

Yet a further object is to provide an improvement in aspirin therapy which permits the administration to a human subject of relatively high therapeutic or pharmaceutically effective dosage of aspirin, without causing any adverse side effects or morbidity.

These and other objects and advantages of the present invention will become evident from the description which follows.

2. Brief Description of the Invention

Within the context of the present invention, it will be understood that the term "vitamin A" or reference to "vitamin A" per se includes and encompasses vitamin A precursors such as B-carotene, which when assimilated into the body yield vitamin A or a derivative thereof, retinol, transretinyl palmitate, or other retinyl esters such as transretinyl acetate, or fish liver oil rich in natural vitamin A.

The present invention basically entails the provision of a development consisting of a method and an aspirin formulation for alleviating the adverse side-effects of taking aspirin, by also ingesting vitamin A (or B-carotene) formulations. It has been found that the vitamin A ingestion has a salutary, beneficial and therapeutic effect in that the vitamin A decreases toxicity, including ulcerogenesis, due to aspirin ingestion. Aspirin per se is a very effective medication with pronounced analgesic properties, including the temporary relief of minor aches and pains, and is widely used (in small amounts) with no ill effects. However, since aspirin is a mild anti-coagulant, it sometimes causes bleeding of stomach ulcers, or aggravates pre-existing conditions of that nature. Thus the concomitant administration of Vitamin A per se to humans taking aspirin is very effective in decreasing toxicity and inhibiting ulcerogenesis and bleeding in the stomach. Also effective is B-carotene, a vitamin A precursor, which when assimilated into the body yields vitamin A or a derivative thereof. Some vitamin A metabolites, such as all transretinoic acid, are not effective.

Thus the present invention is characterized by the provision of a method of reducing, decreasing, or eliminating toxicity and inhibiting ulcerogenesis and bleeding in the stomach of a mammal, due to the ingestion of a pharmaceutically effective concentration or dosage of aspirin, which comprises the concomitant administration to the mammal, by ingestion, of a small but effective amount of vitamin A or a precursor of vitamin A. Generally the mammal is a human subject. In this case, typically the daily dosage of vitamin A or vitamin A equivalent is in the range of about 10,000 to 30,000 I.U. (International Units). Usually, the vitamin A is in the form of transretinyl palmitate, or transretinyl acetate, or the like pharmaceutically effective retinyl esters. In addition, in the case of a human subject, generally the daily dosage of aspirin is in the range of about 0.25 to about 4 tablets every 4 hours, each of the tablets being about 5 grains of U.S.P. analgesic aspirin, an adult dosage being at least one tablet every four hours.

Preferably, the vitamin A or vitamin A precursor is ingested by being blended into edible food, the food being ingested by the mammal. In some instances, the food initially contains a concentration of about 15,000 units of vitamin A and about 6.4 milligrams of B-carotene per kilogram, and the vitamin A is blended into the food at an added concentration of about 45 milligrams of vitamin A equivalent as transretinyl palmitate per kilogram of food. In some cases, the vitamin A precursor is B-carotene. In general, the concomitant administration of Vitamin A or a vitamin A precursor takes place between about one hour before and one hour after the ingestion of the aspirin. However, the aspirin and the vitamin A or vitamin A precursor may be ingested together and at the same time by mammal. In most instances, the vitamin A is in the form of vitamin A per se, retinol, transretinyl palmitate, fish liver oil, or B-carotene.

In one embodiment, the present invention basically entails the provision of a synergistic aspirin formulation characterized by the reduction, decrease, or elimination of toxicity and the inhibiting of ulcerogenesis and bleeding in the stomach of a mammal, so that the ingestion of aspirin by the mammal has negligible adverse side-effects, which comprises aspirin in combination with a small but effective amount of vitamin A or a vitamin A precursor. As mentioned supra, usually the mammal is a human subject, and preferably the daily dosage of the formulation includes vitamin A or vitamin A equivalent in the range of about 10,000 to 30,000 I.U., and a pharmaceutically effective dosage of aspirin. Usually the vitamin A is in the form of transretinyl palmitate, transretinyl acetate, or the like ester. The formulation is preferably ingested by being blended into edible food, the food being ingested by the mammal. A preferred vitamin A precursor is B-carotene, however the vitamin A may be in the form of vitamin A per se, retinol, transretinyl palmitate, fish liver oil, or B-carotene, or other known vitamin A precursor or derivative.

With regard to the terms, phrases, and numerical values stated supra and recited in the claims, certain definitions and explanations of the intent of the terminology should be supplied, as follows:

GLOSSARY OF TERMS

Vitamin A:

Generic term applied to all compounds having vitamin A activity in biological systems. When specific quantities are discussed, such chemical terms as "retinol" and "B-carotene" are employed.

Retinol:

Vitamin A (alcohol). Retinol is also used to include retinyl esters (vitamin A esters), provided that the retinol constituent is considered.

Carotene:

Provitamin A. The present invention assumes that other naturally occurring vitamin A-active carotenoids will be included quantitatively on the basis that they have one half of the biological activity of B-carotene.

International Unit (IU):

0.3 ug retinol (0,344 ug retinyl acetate or 0.55 ug retinyl palmitate), 0.6 ug of B-carotene or 1.2 ug of other vitamin A-active carotenoids.

The majority of man's intake of vitamin A is in the retinyl ester form when he consumes animal products and by-products. Carotenoid vitamin A precursors present in plant foods such as ingested B-carotene are converted to vitamin A mainly in the small intestine during the absorption process. Of the various natural carotenoid vitamin A precursors known, B-carotene has the highest biological activity. Other frequently recognized and valuable ones, but of lower biopotency in natural foods, are other carotenes (a, $\gamma$), the apocarotenals, the monohydroxycarotenes (cryptoxanthin), the monoketo-B-carotenes (echinenone), and mono-epoxy-B-carotenes. B-carotene is technically beta-carotene.

The mechanism of the present invention—by means of which the new result, consisting of the pronounced effectiveness and efficacy of vitamin A in conjunction with aspirin in aspirin therapy, especially in terms of the reduction of high-dose aspirin toxicity, is attained—remains unclear. However, basically the objects of the invention are attained in practice, such as to provide a method and aspirin formulation featuring the concomitant administration of vitamin A to humans taking aspirin, to provide an improvement in aspirin therapy which is very effective in decreasing toxicity and inhibiting ulcerogenesis and bleeding in the stomach.

It may be postulated that ulcerogenesis due to aspirin is thought to result from inhibition of gastric mucus bio-synthesis. Further, and if so, vitamin A and its precursors, compounds known to stimulate mucus synthesis, might inhibit aspirin ulcerogenesis by this mechanism. Much work pioneered by the present applicant has demonstrated beyond a doubt that vitamin A and B-carotene can protect against a variety of stresses and toxic substances. Particularly pertinent to this disclosure is the fact that toxicity of high doses of aspirin, evidenced by stomach ulceration and ischemia in the rat, is substantially reduced by moderate supplements of dietary vitamin A to a diet already containing somewhat more than the recommended minimum dialy requirement of vitamin A. Aspirin can be very irritating to the local gastro-intestinal mucus where the pill comes to rest. Even liquid or powdered aspirin are irritating. The present invention guarantees delivery of a protective dose of vitamin A in conjunction with the aspirin.

It has been known for a long time that severely injured or restrained animals may suddenly develop gastric ulcers; however, ulceration of other parts of the gastrointestinal tract may also occur. Similarly, it has been known that burn, trauma, or other acutely ill paitents may develop ulcers. Because these ulcers can occur in patients with no previous history of ulcer disease, and occur in response to trauma or stress, they are termed "stress ulcers." The relationship of this type of ulcer to the common variety duodenal ulcer is not clear.

In 1968, Martin, a Canadian investigator, found that supplemental vitamin A given to rats prior to their restraint decreased the incidence and severity of ulcerogenesis and ulcer formation. He suggested that vitamin A caused an increase in mucus production (a known reaction of vitamin A) by the stomach, thereby protecting it from the ulcerogenic action of stomach acids. This, however, is only a parital explanation of vitamin A's action.

In the 1970's, evidence from several other sources indicated a role for vitamin A in preventing stress-associated ulcers. In the United States, a group of workers found that ulcers induced by the combined regimen of food deprivation and cortisone administration could be prevented by vitamin A administration. Workers in Germany showed that stress ulcers due to blood loss (and subsequent low blood pressure) could be prevented in rats and pigs by supplemental vitamin A. Chernov, in the United States, showed that vitamin A could prevent stress ulcers in patients who suffered blood loss in accidents. The present applicant and other co-workers showed that vitamin A could decrease stress ulceration and death rates in rats subjected to various types of experimental trauma, and that vitamin A could prevent duodenal ulcers, as well as stress ulcers, in rats fed 3,4 diaminotoluene, a compound previously shown by Selye to be ulcerogenic, and which is chemically related to analgesics such as INDOMETHACIN and acetyl aminophenol. In summary, a number of factors contribute to the causation of stress ulceration, and each factor has its proponents who promote a specific cause. Furthermore, in the case of common variety duodenal ulcers, other causative factors are implicated. However, stress ulceration and its causes are inapposite to aspirin-induced ulcerogenesis and death due to oral ingestion of the chemical aspirin, and the observations supra are not analogous and do not relate to vitamin A's preventive actions with regard to aspirin.

Further, in the 1960's, Wolf and a group at M.I.T. emphasized the necessity of dietary vitamin A for the synthesis of mucus-related materials by gastro-intestinal tract; and when Martin found that vitamin A prevented stress ulceration, he (Martin) attributed this to enhanced mucus synthesis. Thus, Wolf and Martin thought of vitamin A as being required for intracellular synthesis of complex carbohydrates of mucus and related compounds. Although vitamin A is required for these processes in the normal state, we think that the usual amounts of vitamin A may not be sufficient to promote mucoid synthesis during stress and thereby protect the stomach against ulceration. However, in stress, vitamin A may have an even more important role in protecting the mucosa of the stomach from erosion. This role of vitamin A relates to prevention of stress-induced constriction of blood vessels to the stomach that deprives the stomach of blood and the oxygen and nutrients contained in the blood. We suggest that mucus synthesis and secretion by the stomach depend upon the integrity of the synthetic and secretory apparatus of the mucus-secreting cells that line the stomach. In turn, the function of the cells depends on adequate oxygenation. The role of tissue oxygen in preventing stress and other ulceration (demonstrated by many workers) may be related to this phenomenon.

We have made the following important observation and offer the following comments on the observation: Both stress and aspirin toxicity depress circulation to the stomach. Supplemental vitamin A prevents the action of aspirin or restraint stress on deprivation of circulation to the stomach. Even though animals are exposed to stressful or toxic chemicals, they do not show the typical signs of stress if they are given vitamin A. For example, vitamin A permits normal patterns of circulation (as judged by coloration) to persist. This means that in spite of stress, erosion of the mucosa is not speeded up. Additionally, it means that synthesis of required mucoids can occur (a) because vitamin A permits the circulation necessary to supply nutrients needed for cellular integrity and synthetic processes, and (b) the supplemental vitamin A supplies a nutrient required for the specific syntheses of mucus like protective agents. From the results reported based on studies, it is obvious that the vitamin A action can be life-saving. It is, however, accomplished at the expense of other processes. Fortunately, these processes are not essential for survival in controlled environments such as one finds in the laboratory or hospital.

The invention accordingly consists in the combination of elements, arrangement of parts, and series of steps which will be exemplified in the method, formulation, and composition of matter hereinafter described, and of which the scope of application is as elucidated supra and as will be indicated in the appended claims.

DETAILED DESCRIPTION OF THE PREFERRED EMBODIMENTS

Following are examples and results which amply demonstrate the effectiveness of the present method and formulation in accomplishing the reduction of high dose aspirin toxicity by dietary vitamin A. Thus, the following test results are exemplary of the present aspirin therapy improvement, as applied to mammals, and as demonstrated with rats. The antidotal action of vitamin A and B-carotene is clearly apparent.

EXAMPLE I

Aspirin (A) Toxicity: Anidotal Action of Vitamin A (VA) and Carotene (BC), But Not of Trans Retinoic Acid (RA)

Ulcerogenesis due to aspirin is thought to result from inhibition of gastric mucus biosynthesis; if so, VA, RA, and BC, compounds known to stimulate mucus synthesis, should inhibit A ulcerogenesis. Male Sprague-Dawley rats were fed a basal commercial chow that contains 15,000 units of VA and 6.4 mg BC/kg (3×NRC recommendations for normal rats). A, 100 mg daily for 9 days was given by gastric intubation. On day 1 of A treatment, feeding of experimental diets was begun. Five diets (9 rats each) were prepared for the basal chow: Diet 1, unsupplemented chow; Diet 11 had 25 mg RA/kg; Diet 111, 10 mg RA/kg, Diet IV, 90 mg BC/kg; Diet V, 45 mg VA (retinyl palmitate/kg). On the 10th day rats were killed.

| Diet | Appearance of Stomach Mucosa* | | | | | |
|------|--------|--------|--------|--------|--------|--------|
|      | Normal | Eroded | Small Ulcers | Medium Ulcers | Large Ulcers | Bleeding |
| I    | 0 | 0 | 2 | 3 | 1 | 3 |
| II   | 0 | 0 | 0 | 1 | 1 | 7 |
| III  | 0 | 0 | 3 | 2 | 2 | 2 |
| IV   | 3 | 4 | 2 | 0 | 0 | 0 |
| V    | 8 | 0 | 1 | 0 | 0 | 0 |

*Numbers refer to number of animals, not number of ulcers. High doses of RA were toxic and low doses were unexpectedly inactive. VA was very effective; unexpectedly, BC was only moderately active.

EXAMPLE II

Reduction of High Dose Aspirin Toxicity By Dietary Vitamin A

Acute and chronic aspirin poisoning are important health and safety problems; there is therefore a need to develop antidotes having either preventive or therapeutic actions. Because supplemental vitamin A inhibits GI stress ulceration, we studied the influence of vitamin A on aspirin-induced ulcerogenesis. Male S-D rats, BW 350 g, were maintained on commercial chow that contains 2×NRC RDA of vitamin A. Groups of rate (1) maintained on the chow or (2) given chow supplemented with 150,000 units vitamin A/kg diet were studied. Both groups received by gavage 100 mg aspirin b.i.d. for 6 days. Aspirin alone killed 30% of the rats and caused significant morbidity in all, manifested by reduced body weight gain, severe stomach distention, marked thinning of the forestomach, and severe blanching of the stomach wall, together with multiple severe gastric ulceration in all the rats. Vitamin A-supplemented animals had (a) normal stomach wall color, (b) no distention, (c) few and small ulcerations in only half the animals, and (d) no deaths. The mechanism(s) of vitamin A protective action may derive from (1) greater mucus production and secretion by the epithelium, (2) moderation of catecholamine sensitivity of smooth muscle in vascular walls and/or pylorus, or (3) moderation of metabolic effects of catecholamines and adrenal glucocorticoids as these relate to acid production. The vascular and metabolic effects of vitamin A may result from antagonism of aspirin-induced changes in prostaglandin metabolism.

EXAMPLE III

Experiments Involving the Effect of Toxic Doses of Aspirin on Ulceration and Survival of Rats We studied the effect of supplemental vitamin A (trans retinyl palmitate) 50 mg/Kg diet on the aspirin toxicity. In addition, we had two other groups of rats: one received no aspirin or vitamin A supplement, whereas the other received a vitamin A supplement. There were ten rats in each treatment group. There were no deaths and no ulcers in the groups that did not receive the aspirin. Three of 10 animals fed the aspirin died with severe ulceration. Of the surviving aspirin-fed rats (7), six had multiple large ulcers (16), multiple medium ulcers (12), and 12 small ulcers. One of the ten rats had no ulcers. Thus, among the other 9 rats, there were 40 ulcers. In the group given vitamin A in addition to aspirin, there were no deaths, and five were totally free of ulcers. For the group as a whole, there were 19 ulcers (compared to 40), 6 of which were large (compared to 16). Clearly, vitamin A protected rats against the worst aspects of aspirin poisoning.

EXAMPLE IV

| Group | Effect of Aspirin and Supplemental Vitamin A on Stomach Ulceration in S.D. Male Rats | | | | | |
|---|---|---|---|---|---|---|
| | No. of rats with ulcer | Contents + stomach Wt (g) | Stomach Ulcers | | | No. of rats with bleeding, and multiple ulcers |
| | | | Small | Medium | Large | |
| Control | 0 | 3.5 | 0 | 0 | 0 | 0 |
| Aspirin | 9/9 | 19.0 | 2 | 10 | 5 | 3/9 |
| Aspirin + vitamin A | 1/10 | 4.0 | 1 | 0 | 0 | 0 |
| Aspirin + 10 mg retinoic acid | 10/10 | 12.6 | 5 | 6 | 9 | 2/10 |
| Aspirin + 25 mg retinoic acid | 9/9 | 13.3 | 0 | 3 | many | 7/9 |
| Aspirin + B—Carotene | 7/10 | 8.7 | 5 | 0 | 0 | 0 |

EXAMPLE V

| | Effect of Aspirin and Vitamin A Supplement on Thymus and Adrenal Glands of S.D. Male Rats | |
|---|---|---|
| | Weights | |
| Treatment | Thymus (mg) | Adrenal (mg) |
| No aspirin | 376 | 76 |
| Aspirin | 122 | 79 |
| Aspirin + vitamin A | 365 | 77 |
| Aspirin + 10 mg retinoic acid | 124 | 79 |
| Aspirin + 25 mg retinoic acid | 108 | 80 |
| Aspirin + B—Carotene | 328 | 78 |

EXAMPLE VI

| Days after Treatment | Effect of Aspirin and Supplemental Vitamin A on Weight Gain in S.D. Male Rats | | | | | |
|---|---|---|---|---|---|---|
| | Weight Gain (g) | | | | | |
| | 1 | 2 | 3 | 4 | 5 | 6 |
| No aspirin | +5.5 | +8.0 | +10.0 | +8.2 | +15.5 | +17.6 |
| Aspirin | −6.2 | −19.8 | −26.8 | −29.4 | −22. | −22.0 |
| Aspirin + vitamin A | +0.6 | −2.9 | −6.8 | −5.8 | −0.4 | −3.1 |
| Aspirin + 10 mg retinoic acid | −7.7 | −11.8 | −9.6 | −19.4 | −16.2 | −26.4 |
| Aspirin + 25 mg retinoic acid | −15.1 | −35.5 | −43.8 | −46.4 | −28.5 | −38.4 |
| Aspirin + B—Carotene | +1.9 | +1.8 | +1.6 | −1.7 | −3.6 | −5.6 |

Numerous alternatives within the scope of the present invention will occur to those skilled in the art. Thus, although the nub and gist of the present invention as elucidated supra is directed to aspirin per se, the invention is equally and generally applicable to instances involving the administration of other non-steroid analgesics and anti-inflammatory agents, since the mechanism postulated supra for the efficacy and salutary benefits of vitamin A ingestion are equally applicable in the case of these other agents, which are also mild anticoagulants.

A concept within the scope of the present invention involves incorporating vitamin A directly into certain aspirin tablets, e.g. layered tablets or combined tablets, especially for usage by children or infants. In this case, and also in the other embodiments of the invention mentioned supra, a typical formulation may contain about 1 to about 10 units of vitamin A per milligram of aspirin.

It will be appreciated by those skilled in the art that the invention, when contemplating the usage of a vitamin A precursor—ester or the like, intends the usage of those compounds and/or ingredients which preferably yield vitamin A in vivo when ingested.

It will thus be seen that there is provided a method and formulation for the reduction of high dose aspirin oxicity by dietary vitamin A, which achieves the various objects of the invention and which is well adapted to meet the conditions of practical use.

As various possible embodiments might be made of the above invention, and as various changes might be made in the embodiments above set forth, it is to be understood that all matter herein described is to be interpreted as illustrative and not in a limiting sense. Thus, it will be understood by those skilled in the art that although preferred and alternative embodiments have been shown and described in accordance with the Patent Statutes, the invention is not limited thereto or thereby, since the embodiments of the invention particularly disclosed and described herein above are presented merely as an example of the invention. Other embodiments, forms, and modifications of the invention, coming within the proper scope and spirit of the appended claims, will of course readily suggest themselves to those skilled in the art. Thus, while there has been described what is at present considered to be the preferred embodiment of the invention, it will be obvious to those skilled in the art that various changes and modifications may be made therein, without departing from the invention, and it is, therefore, aimed in the appended claims to cover all such changes and modifications as fall within the true spirit and scope of the invention.

What is claimed is:

1. A method for reducing toxicity and inhibiting ulcerogenesis and bleeding in the stomach of a mammal due to the ingestion of aspirin, comprising the concomitant ingestion of an amount of vitamin A or a precursor of vitamin A effective to reduce toxicity and inhibit ulcerogenesis and bleeding in the stomach of a mammal due to the ingestion of aspirin, the amount being such as to provide a daily dosage greater than 10,000 I.U. but less than a toxic amount of vitamin A or vitamin A precursor.

2. The method of claim 1 in which the effective amount of vitamin A or a precursor of vitamin A is such as to provide a daily dosage in the range of 10,000 to 30,000 I.U.

3. An ingestible composition which does not exhibit the adverse side effects caused by the ingestion of aspirin in mammals, comprising aspirin and an amount of vitamin A or vitamin A precursor effective to reduce toxicity and inhibit ulcerogenesis and bleeding in the stomach of a mammal due to the ingestion of aspirin, in which the amount of vitamin A or vitamin A precursor is greater than 1 I.U. per milligram of aspirin but less than a toxic amount of vitamin A or vitamin A precursor.

4. The method of claim 1 or the composition of claim 3 in which said mammal is a human.

5. The composition of claim 3 in which the amount of vitamin A or vitamin A precursor per milligram of aspirin is from 1 to 10 I.U.

6. The method of claim 1 or the composition of claim 3 in which said vitamin A precursoe is B-carotene.

7. The method of claim 1 or the composition of claim 3 in which said vitamin A comprises transretinyl palmitate, transretinyl acetate, or other effective retinyl esters.

8. An ingestible composition which does not exhibit the adverse side effects caused by the ingestion of aspirin in mammals, comprising aspirin in the range of 1.25 to 20 grains of U.S.P. analgesic aspirin and an amount of vitamin A or a precursor of vitamin A effective to reduce the toxicity and inhibit ulcerogenesis and bleeding in the stomach of a mammal due to the ingestion of said aspirin.

9. A method for reducing toxicity and inhibiting ulcerogenesis and bleeding in the stomach of a mammal due to the ingestion of aspirin, comprising the concomitant ingestion of aspirin in the range of 1.25 to 20 U.S.P. analgesic aspirin and an amount of vitamin A or a precursor of vitamin A effective to reduce toxicity and inhibit ulcerogenesis and bleeding in the stomach of a mammal due to the ingestion of said aspirin.

10. The composition of claim 8 or the method of claim 9 in which said mammal is a human.

11. The composition of claim 8 or the method of claim 9 in which the vitamin A is in the form of transretinyl palmitate, transretinyl acetate or other effective retinyl esters.

12. The composition of claim 8 or the method of claim 9 in which said vitamin A precursor is B-carotene.

13. The method of claim 9 in which said concomitant ingestion of an effective amount of vitamin A or a precursor of vitamin A takes place between one hour before and one hour after said ingestion of aspirin.

14. The method of claim 9 in which the effective amount of vitamin A or a precursor of vitamin A is ingested by being blended into food which is ingested by said mammal.

15. The method of claim 9 in which said effective amount of vitamin A or a precursor of vitamin A is such as to provide a daily dosage in the range of 10,000 to 30,000 I.U.

* * * * *